United States Patent
Soppimath et al.

(10) Patent No.: US 12,109,211 B2
(45) Date of Patent: Oct. 8, 2024

(54) HYDRALAZINE COMPOSITIONS AND METHODS

(71) Applicant: Endo Ventures Limited, Dublin (IE)

(72) Inventors: Kumaresh Soppimath, Skillman, NJ (US); Tushar Hingorani, Bridgewater, NJ (US); Hari A. Attluri, Jersey City, NJ (US); Harshil H. Jain, Monmouth Junction, NJ (US)

(73) Assignee: ENDO OPERATIONS LIMITED, Ballsbridge (IE)

( * ) Notice: Subject to any disclaimer, the term of this patent is extended or adjusted under 35 U.S.C. 154(b) by 0 days.

(21) Appl. No.: 18/146,756

(22) Filed: Dec. 27, 2022

(65) Prior Publication Data

US 2023/0201197 A1    Jun. 29, 2023

Related U.S. Application Data

(60) Provisional application No. 63/294,670, filed on Dec. 29, 2021.

(51) Int. Cl.
| | | |
|---|---|---|
| *A61K 31/502* | (2006.01) | |
| *A61K 9/08* | (2006.01) | |
| *A61K 47/10* | (2017.01) | |
| *A61K 47/12* | (2006.01) | |

(52) U.S. Cl.
CPC .............. *A61K 31/502* (2013.01); *A61K 9/08* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | |
|---|---|---|
| 2003/0199512 A1 | 10/2003 | Barbeau |
| 2005/0137198 A1* | 6/2005 | Nelson ............... A61P 9/08 514/248 |
| 2008/0293724 A1 | 11/2008 | Loberg |
| 2013/0004573 A1 | 1/2013 | Rekhi et al. |
| 2013/0331393 A1 | 12/2013 | Lewis et al. |
| 2016/0151368 A1* | 6/2016 | Lewis ............... A61K 9/08 514/248 |
| 2017/0281469 A1 | 10/2017 | D'Amico et al. |

OTHER PUBLICATIONS

Akers, "Sterile Drug Products: Formulation, Packaging, Manufacturing, and Quality", 2010, Informa Healthcare, pp. 29-47 (Year: 2010).*
Osha, "Propylene Glycol", 2021, Occupational Safety and Health Administration, pp. 1-4 (Year: 2021).*

* cited by examiner

*Primary Examiner* — Jeffrey H Murray
*Assistant Examiner* — Madeline E Braun
(74) *Attorney, Agent, or Firm* — ARENTFOX SCHIFF LLP (57) ABSTRACT

A sterile, ready-to-use pharmaceutical composition having hydralazine and/or a salt thereof at a concentration of less than about 20 mg/mL and a solvent comprising an organic co-solvent, wherein the hydralazine and/or salt thereof and the organic co-solvent are provided at a first weight ratio sufficient for the hydralazine and/or salt thereof to have a change in concentration of no more than about 10% after 2 months of storage at 60° C. Also described are methods of making and using the composition.

18 Claims, 2 Drawing Sheets

HYDRALAZINE COMPOSITIONS AND METHODS

CROSS-REFERENCE TO RELATED APPLICATION

This application claims priority to U.S. Patent Application No. 63/294,670, filed Dec. 29, 2021, the entirety of which is incorporated herein by reference.

TECHNICAL FIELD

The present disclosure is directed to stable hydralazine hydrochloride compositions and methods of making and using the same.

BACKGROUND

High blood pressure (i.e., hypertension) is a known risk factor for a variety of conditions. Left untreated, it can lead to significant injury to brain tissue, heart muscles, blood vessels, and the kidneys. In a number of cases, high blood pressure can be reduced by lifestyle changes and changes to nutrition. However, in other cases, high blood pressure may be hereditary or secondary to other conditions (e.g., pregnancy).

Hydralazine is often used in the treatment of hypertension. In an injectable formulation, hydralazine is generally provided in a 20 mg/mL dosage form.

Unfortunately, hydralazine hydrochloride is known for its instability upon storage, particularly when provided as an injectable formation. In particular, when provided in an injectable formulation, hydralazine typically forms small yellow-green particles after periods of storage. In addition, hydralazine hydrochloride injectable formulations often undergo degradation due to the highly reactive hydrazine group, in addition to several other undesirable reactions such as chelation with metal ions, oxidation, and pH-dependent decomposition. Hydralazine is also sensitive to a significant number of excipients that can react with its hydrazine moiety.

In addition, concentrated 20 mg/mL dosage forms of hydralazine for injection are often difficult to administer accurately, especially where relatively low dosages are desired. Therefore, concentrated hydralazine solutions are often diluted prior to administration, which increases the risk for contamination, miscalculation, and metal contamination (leading to rapid hydralazine loss).

SUMMARY

The present disclosure is directed to a sterile, ready-to-use pharmaceutical composition having hydralazine and/or a salt thereof at a first concentration and a solvent having an organic co-solvent, wherein the hydralazine and/or salt thereof and the organic co-solvent are provided at a first weight ratio sufficient for the hydralazine and/or salt thereof to have an acceptable change in concentration after a certain period of shelf life.

DETAILED DESCRIPTION

The present disclosure is directed to a pharmaceutical composition including hydralazine and/or a salt thereof in a solvent, the solvent having one or more co-solvents. According to some aspects, the hydralazine and/or salt thereof and at least one of the co-solvents may be provided in a first weight ratio sufficient for the composition to have an acceptable initial impurity and/or an acceptable impurity level after a certain period of shelf life. The composition may be useful for the treatment of hypertension, hypertensive emergency, eclampsia, heart failure with reduced ejection fraction (HFrEF), or a combination thereof. According to some aspects, the composition may be administrable via an oral dosage form. Additionally or alternatively, the composition may be administrable via subcutaneous, intracameral, intravenous, and/or intramuscular injection, infusion, intra-arterial administration, intracardiac injection, endotracheal administration, intraosseous administration, oral inhalation, topical administration, and as ophthalmic irrigation. The present disclosure is also directed to methods of making and using the compositions described herein.

The composition of the present disclosure includes hydralazine and/or a pharmaceutically acceptable salt thereof as an active agent. Non-limiting examples of pharmaceutically acceptable salts include hydrochloride salts, sodium salts, sulfate salts, acetate salts, phosphate salts, diphosphate salts, chloride salts, potassium salts, maleate salts, calcium salts, citrate salts, mesylate salts, nitrate salts, tartrate salts, aluminum salts, gluconate salts, and combinations thereof. According to some aspects, the composition includes hydralazine hydrochloride.

According to some aspects, the hydralazine and/or a pharmaceutically acceptable salt thereof may be the only active agent included in the composition. However, it should be understood that the composition may include one, two, three, four, or more additional active agents.

According to some aspects, the hydralazine and/or salt thereof may be provided at a concentration sufficient for any of the uses described herein. In one non-limiting example, the hydralazine and/or salt thereof may be provided at a concentration such that the composition is a ready-to-use composition. As used herein, a "ready-to-use" composition refers to a pharmaceutical composition that may be administered to a subject without a preparation step, such as a dilution step.

According to some aspects, the hydralazine and/or salt thereof may be provided at a concentration of less than about 20 mg/mL, optionally less than about 19 mg/mL, optionally less than about 18 mg/mL, optionally less than about 17 mg/mL, optionally less than about 16 mg/mL, optionally less than about 15 mg/mL, optionally less than about 14 mg/mL, optionally less than about 13 mg/mL, optionally less than about 12 mg/mL, optionally less than about 11 mg/mL, optionally less than about 10 mg/mL, optionally less than about 9 mg/mL, optionally less than about 8 mg/mL, optionally less than about 7 mg/mL, optionally less than about 6 mg/mL, optionally less than about 5 mg/mL, optionally less than about 4 mg/mL, optionally less than about 3 mg/mL, optionally less than about 2 mg/mL, and optionally less than about 1 mg/mL.

According to some aspects, the hydralazine and/or salt thereof may be provided at a concentration of about 19 mg/mL, optionally about 18 mg/mL, optionally about 17 mg/mL, optionally about 16 mg/mL, optionally about 15 mg/mL, optionally about 14 mg/mL, optionally about 13 mg/mL, optionally about 12 mg/mL, optionally about 11 mg/mL, optionally about 10 mg/mL, optionally about 9 mg/mL, optionally about 8 mg/mL, optionally about 7 mg/mL, optionally about 6 mg/mL, optionally about 5 mg/mL, optionally about 4 mg/mL, optionally about 3 mg/mL, optionally about 2 mg/mL, and optionally about 1 mg/mL.

According to some aspects, the hydralazine and/or salt thereof may be provided at a concentration of between about 1 and 10 mg/mL, optionally between about 1 and 5 mg/mL, optionally between about 3 and 8 mg/mL, optionally between about 6 and 11 mg/mL, optionally between about 9 and 14 mg/mL, optionally between about 12 and 17 mg/mL, and optionally between about 14 and 19 mg/mL. According to some aspects, the hydralazine and/or salt thereof may be provided at a concentration of between about 1 and 20 mg/mL, optionally between about 5 and 15 mg/mL, optionally between about 6 and 14 mg/mL, optionally between about 3 and 13 mg/mL, optionally between about 8 and 12 mg/mL, optionally between about 9 and 11 mg/mL, and optionally about 10 mg/mL.

The composition may further include a solvent. According to some aspects, the solvent may be acceptable for pharmaceutical administration. Examples of methods of pharmaceutical administration include, but are not limited to, subcutaneous, intracameral, intravenous, and/or intramuscular injection, infusion, intra-arterial administration, intracardiac injection, and preferably, parenteral administration.

The solvent according to the present disclosure may include water, such as water for injection (WFI). As used herein, the term "water for injection" or "WFI" refers to sterile, non-pyrogenic, distilled water suitable for intravenous administration after addition of a suitable solute. According to some aspects, WFI may refer to water that meets USP requirements for WFI. For example, WFI may refer to water that includes less than 0.25 USP Endotoxin Unit/mL per the Bacterial Endotoxins Test <85>, meets the requirements as set forth in Water Conductivity, Bulk Water <645>, and meets the requirements as set forth in Total Organic Carbon <643>.

The solvent according to the present disclosure may further include one or more co-solvents. As used herein, the term "co-solvent" refers to a component of a solvent that is provided at a concentration of less than 50% v/v of the solvent.

Non-limiting examples of co-solvents according to the present disclosure include acetic acid, acetone, acetonitrile, animal oil, aqueous buffer, benzene, bisabolol, butanol, carbon tetrachloride, chlorobenzene, chloroform, dextrose, dimethylformamide, dioxane, essential oil, ethanol, ethyl acetate, ethyl oleate, ethylene chloride, ethylene glycol, fatty acid esters, glycerin, glycofurol, hexane, hydrogenated vegetable oil, isopropanol, isopropyl alcohol, isopropyl myristate, isopropyl palmitate, methanol, methylene chloride, mineral oil, polyethylene glycol, propylene glycol, short-chain polyethylene glycols, silicone fluid glyceride, squalane, terpene, tetrahydrofuran, toluene, triacetin, tributyl citrate, triethyl citrate, vegetable oil, and combinations thereof.

In some examples, the one or more co-solvents of the present disclosure may include an organic component. Example organic components include, but are not limited to, alcohols, polyols, and combinations thereof. For example, the composition of the present disclosure may include one, two, three, four, or more co-solvents, wherein each of the co-solvents is independently selected from ethanol, ethylene glycol, propylene glycol, and short-chain polyethylene glycols. According to some examples, a "short-chain polyethylene glycol" may refer to a polyethylene glycol having an average molecular weight of less than about 2,500 Da, optionally less than about 1,250 Da, and optionally less than about 600 Da. According to some examples, a "short-chain polyethylene glycol" may refer to a polyethylene glycol having an average molecular weight of between about 200 and 2,500 Da, optionally between about 200 and 1250 Da, and optionally between about 200 and 600 Da.

According to some aspects, the solvent may include one co-solvent, two co-solvents, three co-solvents, or more, wherein each of the co-solvents is provided at a concentration of less than 50% v/v of the solvent. For example, each of the co-solvents may be independently provided at a concentration of between about 0.1 and less than 50% v/v, optionally between about 0.1 and 25% v/v, and optionally between about 0.1 and 10% v/v. According to some aspects, each of the co-solvents may be independently provided at a concentration of no more than about 10% v/v, optionally no more than about 9% v/v, optionally no more than about 8% v/v, optionally no more than about 7% v/v, optionally no more than about 6% v/v, optionally no more than about 5% v/v, optionally no more than about 4% v/v, optionally no more than about 3% v/v, optionally no more than about 2% v/v, and optionally no more than about 1% v/v. According to some aspects, each of the co-solvents may be independently provided at a concentration of about 10% v/v, optionally about 9% v/v, optionally about 8% v/v, optionally about 7% v/v, optionally about 6% v/v, optionally about 5% v/v, optionally about 4% v/v, optionally about 3% v/v, optionally about 2% v/v, and optionally about 1% v/v.

According to some aspects, a total concentration of co-solvents in the composition may be less than 50% v/v of the solvent. For example, a total concentration of co-solvents in the composition may be between about 0.1 and 50% v/v, optionally between about 0.1 and 25% v/v, and optionally between about 0.1 and 10% v/v. According to some aspects, a total concentration of co-solvents in the composition may be no more than about 10% v/v, optionally no more than about 9% v/v, optionally no more than about 8% v/v, optionally no more than about 7% v/v, optionally no more than about 6% v/v, optionally no more than about 5% v/v, optionally no more than about 4% v/v, optionally no more than about 3% v/v, optionally no more than about 2% v/v, and optionally no more than about 1% v/v. According to some aspects, a total concentration of co-solvents may be about 10% v/v, optionally about 9% v/v, optionally about 8% v/v, optionally about 7% v/v, optionally about 6% v/v, optionally about 5% v/v, optionally about 4% v/v, optionally about 3% v/v, optionally about 2% v/v, and optionally about 1% v/v.

According to some aspects, each of the co-solvents may be independently provided at a concentration of no more than about 50 mg/mL, optionally no more than about 40 mg/mL, optionally no more than about 30 mg/mL, optionally no more than about 20 mg/mL, and optionally no more than about 10 mg/ml.

According to some aspects, a total concentration of co-solvents in the composition may be provided at a concentration of no more than about 50 mg/mL, optionally no more than about 40 mg/mL, optionally no more than about 30 mg/mL, optionally no more than about 20 mg/mL, and optionally no more than about 10 mg/ml.

According to some aspects, the hydralazine and/or salt thereof and at least one of the co-solvents may be provided in a first weight ratio such that the composition has an acceptable initial impurity level and/or an acceptable impurity level after a certain period of shelf life.

As used herein, the term "impurity" refers to an undesired substance in a composition. It should be understood that one or more impurities may be present in an initial composition and/or may be formed after a certain period of shelf life of a composition. For example, one or more impurities may be formed via degradation of one or more components of the composition, such as the hydralazine and/or salt thereof. Sources of degradation include, but are not limited to, chelation with metal ions, oxidation, racemization, visible light, ultraviolet light, moisture, heat (including heat from a sterilization process), changes in pH, and composition component interactions.

Example impurities as described herein include, but are not limited to, phthalazine, phthalazone, 2-carboxybenzalehyde-2, and 2-carboxybenzalehyde-1. Additionally or alternatively, the impurities according to the present disclosure may include unknown impurities. Example unknown impurities according to the present disclosure include Impurity A, B, C, D, E, F, G, H, I, and/or J as described in Example I.

According to some aspects, the composition may have no more than about 20% of total impurities after a certain period of shelf life, preferably no more than about 19.5%, more preferably no more than about 19%, more preferably no more than about 18.5%, preferably no more than about 18%, more preferably no more than about 17.5%, more preferably no more than about 17%, more preferably no more than about 16.5%, more preferably no more than about 16%, more preferably no more than about 15.5%, more preferably no more than about 15%, more preferably no more than about 14.5%, more preferably no more than about 14%, more preferably no more than about 13.5%, more preferably no more than about 13%, more preferably no more than about 12.5%, more preferably no more than about 12%, more preferably no more than about 11.5%, more preferably no more than about 11%, more preferably no more than about 10.5%, more preferably no more than about 10%, more preferably no more than about 9.5%, more preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, and most preferably no more than about 5%.

According to some aspects, the composition may have no more than about 20% of total impurities after a certain period of shelf life, preferably no more than about 19.9%, more preferably no more than about 19.8%, more preferably no more than about 19.7%, more preferably no more than about 19.6%, more preferably no more than about 19.5%, more preferably no more than about 19.4%, more preferably no more than about 19.3%, more preferably no more than about 19.2%, more preferably no more than about 19.1%, more preferably no more than about 19%, more preferably no more than about 18.9%, more preferably no more than about 18.8%, more preferably no more than about 18.7%, more preferably no more than about 18.6%, more preferably no more than about 18.5%, more preferably no more than about 18.4%, more preferably no more than about 18.3%, more preferably no more than about 18.2%, more preferably no more than about 18.1%, more preferably no more than about 18%, more preferably no more than about 17.9%, more preferably no more than about 17.8%, more preferably no more than about 17.7%, more preferably no more than about 17.6%, more preferably no more than about 17.5%, more preferably no more than about 17.4%, more preferably no more than about 17.3%, more preferably no more than about 17.2%, more preferably no more than about 17.1%, more preferably no more than about 17%, more preferably no more than about 16.9%, more preferably no more than about 16.8%, more preferably no more than about 16.7%, more preferably no more than about 16.6%, more preferably no more than about 16.5%, more preferably no more than about 16.4%, more preferably no more than about 16.3%, more preferably no more than about 16.2%, more preferably no more than about 16.1%, more preferably no more than about 16%, more preferably no more than about 15.9%, more preferably no more than about 15.8%, more preferably no more than about 15.7%, more preferably no more than about 15.6%, more preferably no more than about 15.5%, more preferably no more than about 15.4%, more preferably no more than about 15.3%, more preferably no more than about 15.2%, more preferably no more than about 15.1%, more preferably no more than about 15%, more preferably no more than about 14.9%, more preferably no more than about 14.8%, more preferably no more than about 14.7%, more preferably no more than about 14.6%, more preferably no more than about 14.5%, more preferably no more than about 14.4%, more preferably no more than about 14.3%, more preferably no more than about 14.2%, more preferably no more than about 14.1%, more preferably no more than about 14%, more preferably no more than about 13.9%, more preferably no more than about 13.8%, more preferably no more than about 13.7%, more preferably no more than about 13.6%, more preferably no more than about 13.5%, more preferably no more than about 13.4%, more preferably no more than about 13.3%, more preferably no more than about 13.2%, more preferably no more than about 13.1%, more preferably no more than about 13%, more preferably no more than about 12.9%, more preferably no more than about 12.8%, more preferably no more than about 12.7%, more preferably no more than about 12.6%, more preferably no more than about 12.5%, more preferably no more than about 12.4%, more preferably no more than about 12.3%, more preferably no more than about 12.2%, more preferably no more than about 12.1%, more preferably no more than about 12%, more preferably no more than about 11.9%, more preferably no more than about 11.8%, more preferably no more than about 11.7%, more preferably no more than about 11.6%, more preferably no more than about 11.5%, more preferably no more than about 11.4%, more preferably no more than about 11.3%, more preferably no more than about 11.2%, more preferably no more than about 11.1%, more preferably no more than about 11%, more preferably no more than about 10.9%, more preferably no more than about 10.8%, more preferably no more than about 10.7%, more preferably no more than about 10.6%, more preferably no more than about 10.5%, more preferably no more than about 10.4%, more preferably no more than about 10.3%, more preferably no more than about 10.2%, more preferably no more than about 10.1%, more preferably no more than about 10%, more preferably no more than about 9.9%, more preferably no more than about 9.8%, more preferably no more than about 9.7%, more preferably no more than about 9.6%, more preferably no more than about 9.5%, more preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, and most preferably about 0%.

According to some aspects, a concentration of each impurity described herein may independently be no more than about 20% after a certain period of shelf life, preferably no more than about 19.5%, more preferably no more than about 19%, more preferably no more than about 18.5%, preferably no more than about 18%, more preferably no more than about 17.5%, more preferably no more than about 17%, more preferably no more than about 16.5%, more preferably no more than about 16%, more preferably no more than about 15.5%, more preferably no more than about 15%, more preferably no more than about 14.5%, more preferably no more than about 14%, more preferably no more than about 13.5%, more preferably no more than about 13%, more preferably no more than about 12.5%, more preferably no more than about 12%, more preferably no more than about 11.5%, more preferably no more than about 11%, more preferably no more than about 10.5%, more preferably no more than about 10%, more preferably no more than about 9.5%, more preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, and most preferably no more than about 5%.

According to some aspects, a concentration of each impurity described herein may independently be no more than about 20% after a certain period of shelf life, preferably no more than about 19.9%, more preferably no more than about 19.8%, more preferably no more than about 19.7%, more preferably no more than about 19.6%, more preferably no more than about 19.5%, more preferably no more than about 19.4%, more preferably no more than about 19.3%, more preferably no more than about 19.2%, more preferably no more than about 19.1%, more preferably no more than about 19%, more preferably no more than about 18.9%, more preferably no more than about 18.8%, more preferably no more than about 18.7%, more preferably no more than about 18.6%, more preferably no more than about 18.5%, more preferably no more than about 18.4%, more preferably no more than about 18.3%, more preferably no more than about 18.2%, more preferably no more than about 18.1%, more preferably no more than about 18%, more preferably no more than about 17.9%, more preferably no more than about 17.8%, more preferably no more than about 17.7%, more preferably no more than about 17.6%, more preferably no more than about 17.5%, more preferably no more than about 17.4%, more preferably no more than about 17.3%, more preferably no more than about 17.2%, more preferably no more than about 17.1%, more preferably no more than about 17%, more preferably no more than about 16.9%, more preferably no more than about 16.8%, more preferably no more than about 16.7%, more preferably no more than about 16.6%, more preferably no more than about 16.5%, more preferably no more than about 16.4%, more preferably no more than about 16.3%, more preferably no more than about 16.2%, more preferably no more than about 16.1%, more preferably no more than about 16%, more preferably no more than about 15.9%, more preferably no more than about 15.8%, more preferably no more than about 15.7%, more preferably no more than about 15.6%, more preferably no more than about 15.5%, more preferably no more than about 15.4%, more preferably no more than about 15.3%, more preferably no more than about 15.2%, more preferably no more than about 15.1%, more preferably no more than about 15%, more preferably no more than about 14.9%, more preferably no more than about 14.8%, more preferably no more than about 14.7%, more preferably no more than about 14.6%, more preferably no more than about 14.5%, more preferably no more than about 14.4%, more preferably no more than about 14.3%, more preferably no more than about 14.2%, more preferably no more than about 14.1%, more preferably no more than about 14%, more preferably no more than about 13.9%, more preferably no more than about 13.8%, more preferably no more than about 13.7%, more preferably no more than about 13.6%, more preferably no more than about 13.5%, more preferably no more than about 13.4%, more preferably no more than about 13.3%, more preferably no more than about 13.2%, more preferably no more than about 13.1%, more preferably no more than about 13%, more preferably no more than about 12.9%, more preferably no more than about 12.8%, more preferably no more than about 12.7%, more preferably no more than about 12.6%, more preferably no more than about 12.5%, more preferably no more than about 12.4%, more preferably no more than about 12.3%, more preferably no more than about 12.2%, more preferably no more than about 12.1%, more preferably no more than about 12%, more preferably no more than about 11.9%, more preferably no more than about 11.8%, more preferably no more than about 11.7%, more preferably no more than about 11.6%, more preferably no more than about 11.5%, more preferably no more than about 11.4%, more preferably no more than about 11.3%, more preferably no more than about 11.2%, more preferably no more than about 11.1%, more preferably no more than about 11%, more preferably no more than about 10.9%, more preferably no more than about 10.8%, more preferably no more than about 10.7%, more preferably no more than about 10.6%, more preferably no more than about 10.5%, more preferably no more than about 10.4%, more preferably no more than about 10.3%, more preferably no more than about 10.2%, more preferably no more than about 10.1%, more preferably no more than about 10%, more preferably no more than about 9.9%, more preferably no more than about 9.8%, more preferably no more than about 9.7%, more preferably no more than about 9.6%, more preferably no more than about 9.5%, more preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, more preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, and most preferably about 0%.

According to some aspects, the concentration of impurities present in the composition after a certain period of shelf life may be such that the composition does not undergo a physical change. Examples of physical change include, but are not limited to, color change and/or insoluble particle formation.

Unless indicated otherwise, the percentages of impurities expressed herein are expressed as % (w/w) of the active agent.

According to some aspects, the hydralazine and/or salt thereof and at least one of the co-solvents may be provided in a first weight ratio such that the composition shows an acceptable change in the concentration of hydralazine and/or salt thereof after a certain period of shelf. It should be understood that the change in the concentration of hydralazine and/or salt thereof may be related to the degradation of the hydralazine and/or salt thereof during shelf life. Sources of degradation include, but are not limited to, chelation with metal ions, oxidation, racemization, visible light, ultraviolet light, moisture, heat (including heat from a sterilization process), changes in pH, and composition component interactions.

According to some aspects, the composition may show a change in concentration of hydralazine and/or salt thereof of no more than about 20% after a certain period of shelf life, preferably no more than about 19.5%, more preferably no more than about 19%, more preferably no more than about 18.5%, preferably no more than about 18%, more preferably no more than about 17.5%, more preferably no more than about 17%, more preferably no more than about 16.5%, more preferably no more than about 16%, more preferably no more than about 15.5%, more preferably no more than about 15%, more preferably no more than about 14.5%, more preferably no more than about 14%, more preferably no more than about 13.5%, more preferably no more than about 13%, more preferably no more than about 12.5%, more preferably no more than about 12%, more preferably no more than about 11.5%, more preferably no more than about 11%, more preferably no more than about 10.5%, more preferably no more than about 10%, more preferably no more than about 9.5%, more preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, and most preferably no more than about 5%.

According to some aspects, the composition may show a change in concentration of hydralazine and/or salt thereof of no more than about 20% after a certain period of shelf life, preferably no more than about 19.9%, more preferably no more than about 19.8%, more preferably no more than about 19.7%, more preferably no more than about 19.6%, more preferably no more than about 19.5%, more preferably no more than about 19.4%, more preferably no more than about 19.3%, more preferably no more than about 19.2%, more preferably no more than about 19.1%, more preferably no more than about 19%, more preferably no more than about 18.9%, more preferably no more than about 18.8%, more preferably no more than about 18.7%, more preferably no more than about 18.6%, more preferably no more than about 18.5%, more preferably no more than about 18.4%, more preferably no more than about 18.3%, more preferably no more than about 18.2%, more preferably no more than about 18.1%, more preferably no more than about 18%, more preferably no more than about 17.9%, more preferably no more than about 17.8%, more preferably no more than about 17.7%, more preferably no more than about 17.6%, more preferably no more than about 17.5%, more preferably no more than about 17.4%, more preferably no more than about 17.3%, more preferably no more than about 17.2%, more preferably no more than about 17.1%, more preferably no more than about 17%, more preferably no more than about 16.9%, more preferably no more than about 16.8%, more preferably no more than about 16.7%, more preferably no more than about 16.6%, more preferably no more than about 16.5%, more preferably no more than about 16.4%, more preferably no more than about 16.3%, more preferably no more than about 16.2%, more preferably no more than about 16.1%, more preferably no more than about 16%, more preferably no more than about 15.9%, more preferably no more than about 15.8%, more preferably no more than about 15.7%, more preferably no more than about 15.6%, more preferably no more than about 15.5%, more preferably no more than about 15.4%, more preferably no more than about 15.3%, more preferably no more than about 15.2%, more preferably no more than about 15.1%, more preferably no more than about 15%, more preferably no more than about 14.9%, more preferably no more than about 14.8%, more preferably no more than about 14.7%, more preferably no more than about 14.6%, more preferably no more than about 14.5%, more preferably no more than about 14.4%, more preferably no more than about 14.3%, more preferably no more than about 14.2%, more preferably no more than about 14.1%, more preferably no more than about 14%, more preferably no more than about 13.9%, more preferably no more than about 13.8%, more preferably no more than about 13.7%, more preferably no more than about 13.6%, more preferably no more than about 13.5%, more preferably no more than about 13.4%, more preferably no more than about 13.3%, more preferably no more than about 13.2%, more preferably no more than about 13.1%, more preferably no more than about 13%, more preferably no more than about 12.9%, more preferably no more than about 12.8%, more preferably no more than about 12.7%, more preferably no more than about 12.6%, more preferably no more than about 12.5%, more preferably no more than about 12.4%, more preferably no more than about 12.3%, more preferably no more than about 12.2%, more preferably no more than about 12.1%, more preferably no more than about 12%, more preferably no more than about 11.9%, more preferably no more than about 11.8%, more preferably no more than about 11.7%, more preferably no more than about 11.6%, more preferably no more than about 11.5%, more preferably no more than about 11.4%, more preferably no more than about 11.3%, more preferably no more than about 11.2%, more preferably no more than about 11.1%, more preferably no more than about 11%, more preferably no more than about 10.9%, more preferably no more than about 10.8%, more preferably no more than about 10.7%, more preferably no more than about 10.6%, more preferably no more than about 10.5%, more preferably no more than about 10.4%, more preferably no more than about 10.3%, more preferably no more than about 10.2%, more preferably no more than about 10.1%, more preferably no more than about 10%, more preferably no more than about 9.9%, more preferably no more than about 9.8%, more preferably no more than about 9.7%, more preferably no more than about 9.6%, more preferably no more than about 9.5%, more preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, more preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, and most preferably about 0%.

Unless indicated otherwise, the percentages of change in concentration of hydralazine and/or salt thereof are expressed as % (w/w).

As used throughout this application, the term "shelf life" refers to the length of time that a product may be stored without becoming unfit for medical use. Examples of compositions which are unfit for medical use include, but are not limited to, compositions with unacceptably high impurity levels and/or the presence of physical changes as described herein.

The period of shelf life of the composition may be 1 month, preferably 2 months, more preferably 3 months, more preferably 4 months, more preferably 5 months, more preferably 6 months, more preferably 7 months, more preferably 8 months, more preferably 9 months, more preferably 10 months, more preferably 11 months, more 12 months, preferably 13 months, more preferably 14 months, more preferably 15 months, more preferably 16 months, more preferably 17 months, more preferably 18 months, more preferably 19 months, more preferably 20 months, more preferably 21 months, more preferably 22 months, more preferably 23 months, more preferably 24 months, more preferably 25 months, more preferably 26 months, more preferably 27 months, more preferably 28 months, more preferably 29 months, more preferably 30 months, more preferably 31 months, more preferably 32 months, more preferably 33 months, more preferably 34 months, more preferably 35 months, and most preferably 36 months. According to some aspects, the period of shelf life may vary based on product presentation.

According to some aspects, shelf life may be determined by measuring certain characteristics of the composition that may indicate that the composition is unfit for medical use. According to some aspects, shelf life may be determined by measuring the concentration of impurities in the composition after storage at 5° C.±3° C. According to some aspects, shelf life may be determined by measuring the concentration of impurities in the composition after storage at 25° C.±5° C. According to some aspects, shelf life may be determined by measuring the concentration of impurities in the composition after storage at 40° C.±5° C. According to some aspects, shelf life may be determined by measuring the concentration of impurities in the composition after storage at 60° C.±5° C. According to some aspects, shelf life may be determined by assaying the amount of the active ingredient still present in its unaltered form.

According to some aspects, shelf life may be determined by measuring certain characteristics of the composition that may indicate that the composition is unfit for medical use. According to some aspects, shelf life may be determined by measuring the concentration of impurities in the composition after storage at 5° C.±3° C. at 40% RH±10% RH. According to some aspects, shelf life may be determined by measuring the concentration of impurities in the composition after storage at 25° C.±5° C. at 60% RH±5% RH. According to some aspects, shelf life may be determined by measuring the concentration of impurities in the composition after storage at 40° C.±5° C. at 65% RH±5% RH. According to some aspects, shelf life may be determined by measuring the concentration of impurities in the composition after storage at 60° C.±5° C. at 70% RH±5% RH. According to some aspects, shelf life may be determined by assaying the amount of the active ingredient still present in its unaltered form.

In some non-limiting examples, shelf life may be determined for refrigerated, long term, intermediate, and/or accelerated storage conditions by measuring the concentration of impurities after storage in the conditions shown in Table 1, wherein the composition is packaged in a container closure system that is the same as or simulates the packaging proposed for storage and distribution.

TABLE 1

| Storage Conditions | |
|---|---|
| Study | Storage condition |
| Refrigerated | 5° C. ± 3° C./40% RH ± 10% RH |
| Long term | 25° C. ± 5° C./60% RH ± 5% RH |
| Intermediate | 40° C. ± 5° C./65% RH ± 5% RH |
| Accelerated | 60° C. ± 5° C./70% RH ± 5% RH |

According to some aspects, shelf life may be attributed at least in part to the concentration of impurities in the composition such that the reduction of impurity concentration and/or rate of impurity formation lengthens the composition's shelf life.

According to some aspects, the weight ratio of at least one of the co-solvents to the hydralazine and/or salt thereof in the composition may be no more than about 7.5:1, optionally no more than about 7:1, optionally no more than about 6.5:1, optionally no more than about 6:1, optionally no more than about 5.5:1, optionally no more than about 5:1, optionally no more than about 4.5:1, optionally no more than about 4:1, optionally no more than about 3.5:1, optionally no more than about 3:1, optionally no more than about 2.5:1, optionally no more than about 2:1, optionally no more than about 1.5:1, and optionally no more than about 1:1.

According to some aspects, the weight ratio of at least one of the co-solvents to the hydralazine and/or salt thereof in the composition may be between about 1:1 and 7.5:1, optionally between about 1:1 and 7:1, optionally between about 1:1 and 6.5:1, optionally between about 1:1 and 6:1, optionally between about 1:1 and 5.5:1, and optionally between about 1:1 and 5:1.

According to some aspects, the weight ratio of at least one of the co-solvents to the hydralazine and/or salt in the composition thereof may be about 7.5:1, optionally about 7:1, optionally about 6.5:1, optionally about 6:1, optionally about 5.5:1, optionally about 5:1, optionally about 4.5:1, optionally about 4:1, optionally about 3.5:1, optionally about 3:1, optionally about 2.5:1, optionally about 2:1, optionally about 1.5:1, and optionally about 1:1.

According to some aspects, the weight ratio of all co-solvents to the hydralazine and/or salt thereof in the composition may be no more than about 7.5:1, optionally no more than about 7:1, optionally no more than about 6.5:1, optionally no more than about 6:1, optionally no more than about 5.5:1, optionally no more than about 5:1, optionally no more than about 4.5:1, optionally no more than about 4:1, optionally no more than about 3.5:1, optionally no more than about 3:1, optionally no more than about 2.5:1, optionally no more than about 2:1, optionally no more than about 1.5:1, and optionally no more than about 1:1.

According to some aspects, the weight ratio of all co-solvents to the hydralazine and/or salt thereof in the composition may be between about 1:1 and 7.5:1, optionally between about 1:1 and 7:1, optionally between about 1:1 and 6.5:1, optionally between about 1:1 and 6:1, optionally between about 1:1 and 5.5:1, and optionally between about 1:1 and 5:1.

According to some aspects, the weight ratio of all co-solvents to the hydralazine and/or salt thereof in the composition may be about 7.5:1, optionally about 7:1, optionally about 6.5:1, optionally about 6:1, optionally about 5.5:1, optionally about 5:1, optionally about 4.5:1, optionally about 4:1, optionally about 3.5:1, optionally about 3:1, optionally about 2.5:1, optionally about 2:1, optionally about 1.5:1, and optionally about 1:1.

According to some aspects, the composition may further include a buffer system having one or more buffer components. As used herein, the term "buffer system" refers to a component of a composition that provides a resistance to significant change in pH caused by a strong acid or base. A buffer system may include two or more buffer components, such as a weak acid and its conjugate base. A buffer system may provide a resistance to a significant pH change by interacting with a strong acid or strong base in a composition or solution, thereby at least partially preventing the pH of the composition or solution from changing significantly.

Generally, a buffer system has one or more buffer ranges wherein the buffer system has the ability to provide resistance to significant pH change. When a composition or solution comprising the buffer system has a pH inside the buffer system's buffer range, the pH of the composition or solution will not change significantly with the addition of equimolar amounts of a strong acid or strong base.

The buffer range of a buffer system is related to the acid dissociation constant ($K_a$) of one or more weak acids included by the buffer system. The term "acid dissociation constant" refers to the equilibrium constant of a dissociation reaction of an acid. The midpoint of a buffer range for a buffer system is generally about the logarithmic measure of the acid dissociation constant (i.e., the pKa, equal to $-\log_{10} K_a$) of a weak acid included by the buffer system.

According to some aspects, the buffer system may include one or more buffer components having one or more $pK_a$ values. The one or more buffer components may include a $pK_a$ value that is within +/−1 unit of the initial pH of the composition in the form of a solution without the pH raising agent. According to some aspects, the one or more buffer components may have a $pK_a$ value within the range of no more than about 7, optionally no more than about 6, optionally no more than about 5. According to some aspects, the one or more buffer components may have a $pK_a$ value within the range of about 2 to 5, optionally within the range of about 3 to 5, optionally within the range of about 3.5 to 4.5, optionally between about 4 and 4.5, and optionally between about 4 and 4.2.

The one or more buffer components may provide a resistance to a significant change in pH that other components of the composition may otherwise cause in the absence of the one or more buffer components. For example, the one or more buffer components may provide a resistance to the composition's pH being significantly lowered by degradants and/or reaction products of other components of the composition.

According to some aspects, each of the one or more buffer components may be present in the composition at a concentration in the range of no more than about 100 mM, optionally no more than about 50 mM, optionally no more than about 25 mM, optionally no more than about 20 mM, optionally no more than about 15 mM, optionally no more than about 10 mM, and optionally no more than about 5 mM.

According to some aspects, each of the one or more buffer components may be present in the composition at a concentration in the range of between about 1 and 50 mM, optionally between about 1 and 20 mM, optionally between about 5 and 15 mM, and optionally about 10 mM.

According to some aspects, a total concentration of buffer components in the composition may be in the range of no more than about 100 mM, optionally no more than about 50 mM, optionally no more than about 25 mM, optionally no more than about 20 mM, optionally no more than about 15 mM, optionally no more than about 10 mM, and optionally no more than about 5 mM.

According to some aspects, a total concentration of buffer components in the composition may be in the composition at a concentration in the range of between about 1 and 50 mM, optionally between about 1 and 20 mM, optionally between about 5 and 15 mM, and optionally about 10 mM.

The one or more buffer components may be present at a concentration that provides a resistance to a significant change in the composition's pH despite physical and chemical changes of the composition after a certain period of shelf life as described herein. As used herein, a significant change in pH may be more than 5 pH units, optionally more than 4.5 pH units, optionally more than 4 pH units, optionally more than 3.5 pH units, optionally more than 3 pH units, optionally more than 2.5 pH units, optionally more than 2 pH units, optionally more than 1.5 pH units, optionally more than 1 pH units, and optionally more than 0.5 pH units.

The one or more buffer components may be suitable for oral, subcutaneous, intracameral, intramuscular, parenteral, and/or ophthalmic use.

According to some aspects, the one or more buffer components may include the acids or salt forms of one or more of lactate, tartarate, glutamate, malate, citrate, gluconate, benzoate, succinate, acetate, glycine, and aspartate. According to some aspects, the one or more buffer components may include lithium hydroxide, sodium hydroxide, potassium hydroxide, rubidium hydroxide, cesium hydroxide, calcium hydroxide, strontium hydroxide, sodium phosphate dibasic dihydrate, and/or barium hydroxide.

According to some aspects, the composition may include at least one chelating agent. As used herein, the term "chelating agent" refers to a substance capable of chelation, i.e., the formation or presence of two or more separate coordinate bonds between a polydentate ligand and a single central atom. The chelating agent may be provided at a concentration sufficient to reduce the catalytic activity of trace metals present in the composition. For example, the chelating agent may chelate trace metals in the composition that may otherwise increase and/or accelerate the degradation of components in the composition. Examples of trace metals include, but are not limited to, iron, magnesium, lithium, zinc, copper, chromium, nickel, cobalt, vanadium, arsenic, molybdenum, manganese, selenium, and calcium.

Examples of chelating agents include, but are not limited to, bicarboxylic acids, tricarboxylic acids, aminopolycarboxylic acids, and combinations thereof. According to some aspects, the chelating agent may include one or more of TPA (Tris[(2-pyridyl)methyl]amine), phanquinone (4,7-phenanthroline-5,6-dione), clioquinol (PN Gerolymatos SA), chloroquinol, penicillamine, trientine, N,N'-diethyldithiocarbamate (DDC), 2,3,2'-tetraamine (2,3,2'-tet), neocuproine, N,N,N',N'-tetrakis(2-pyridylmethyl) ethylenediamine (TPEN), 1,10-phenanthroline (PHE), tetraethylenepentamine (TEPA), triethylene tetraamine and tris(2-carboxyethyl)phosphine (TCEP), bathophenanthroline disulfonic acid (BPADA), Disodium Edetate Dihydrate (EDTA), ethylene glycol (bis) aminoethyl ether tetra acetic acid (EGTA), nitrilotriacetic acid, TIRON™, N,N-bis(2-hydroxyethyl)glycine (bicine), O,O'-bis(2-aminophenyl ethylene glycol) ethylenediamine-N,N,N',N'-tetraacetic acid (BAPTA), trans-1,2-diamino cyclohexane-ethylenediamine-N,N,N',N'-tetraacetic acid (CyDTA), 1,3-diamino-2-hydroxy-propane-ethylenediamine-N,N,N', N'-tetraacetic acid (DPTA-OH), ethylene-diamine-N,N'-dipropionic acid dihydrochloride (EDDP), ethylenediamine-N,N'-bis(methylenephosphonic acid) hemihydrate (EDDPO), ethylenediamine-N,N,N',N'-tetrakis(methylenephosphonic acid) (EDTPO), N,N'-bis(2-hydroxybenzyl)ethylene diamine-N,N'-diacetic acid (HBED), 1,6-hexamethylenediamine-N,N,N',N'-tetraacetic acid (HDTA, or HEDTA), N-(2-hydroxyethyl)iminodiacetic acid (HIDA), iminodiacetic acid (IDA), 1,2-diaminopropane-N,N,N',N'-tetraacetic acid (methyl-EDTA), nitriltriacetic acid (NTA), nitrilotripropionic acid (NTP), nitrilotris (methylenephosphonic acid) trisodium salt (NTPO), triethylenetetramine-N,N,N',N'',N''-hexaacetic acid (TTHA), bathocuproine, penta(carboxymethyl)diethylenetriamine (DTPA), bathophenanthroline, TETA, citric acid, salicylic acid, and/or malic acid, including analogues, derivatives, and pharmaceutically acceptable salts thereof.

According to some aspects, the composition may include at least one tonicity adjusting agent. The term "tonicity" refers to the effective osmotic pressure equivalent of a solution or composition. According to some aspects, the tonicity adjusting agent may be present in the composition at a concentration sufficient to maintain the osmolality of the composition in a physiologically acceptable range, such as between about 260 to 340 mOsm/kg.

Example tonicity adjusting agents include, but are not limited to, glucose, glycerin, hydroxypropyl methyl cellulose, mannitol, polysorbate, propylene glycol, sodium bromide, sodium chloride, sodium iodide, sorbitol, urea, xylitol, and combinations thereof.

According to some aspects, the tonicity adjusting agent may be provided in the composition at a concentration of between about 0.01 and 5 wt %, optionally between about 0.01 and 2.5 wt %, optionally between about 0.6 and 1.2 wt %, optionally between about 0.7 and 1.2 wt %, optionally between about 0.8 and 1.2 wt %, optionally between about 0.9 and 1.2 wt %, and optionally between about 1 and 1.2 wt %.

It should be understood, however, that the examples of each of the active agents, solvents, co-solvents, buffer components, chelating agents, and tonicity adjusting agents as described herein are not necessarily limited to a single function. That is, each of the examples described herein may function as one of an active agent, a solvent, a co-solvent, a buffer component, a chelating agent, and a tonicity adjusting agent as described herein or as a combination of two, three, four, or more functions.

According to some aspects, the composition may be contained in a container. In some non-limiting examples, the container may include a vial, a bag, a bottle, and a pre-filled syringe. In some examples, the pre-filled syringe may include a plunger stopper, a barrel, a needle adapter, a needle hub, and a needle suitable for injection. According to some aspects, the container may include glass, rubber, plastic, or a combination thereof, such as a glass barrel and a rubber plunger stopper. The container may be single-use or multi-use as known in the art.

The container according to the present disclosure may have a labeled size. As used herein, the term "labeled size" refers to the container's pharmaceutical composition holding capacity and is equal to the volume of a composition containable in the container. The container may have a labeled size of between about 0.5 and 10.5 mL, optionally between about 1 and 5 mL, optionally between about 0.5 and 5 mL. According to some aspects, the container may have a labeled size of about 0.5 mL, optionally about 1 mL, optionally about 1.5 mL, optionally about 2 mL, optionally about 2.5 mL, optionally about 3 mL, optionally about 3.5 mL, optionally about 4 mL, optionally about 4.5 mL, optionally about 5 mL, optionally about 5.5 mL, optionally about 6 mL, optionally about 6.5 mL, optionally about 7 mL, optionally about 7.5 mL, optionally about 8 mL, optionally about 8.5 mL, optionally about 9 mL, optionally about 9.5 mL, optionally about 10 mL, and optionally about 10.5 mL.

According to some aspects, the composition is sterile. As used herein, "sterile" refers to meeting sterility requirements for consumption and/or injection into the human body. According to some aspects, sterility may require passing results when measured via the membrane filtration method and/or direct inoculation method as set forth in USP chapter <71>.

The present disclosure is also directed to methods of making the compositions described herein. The method may include providing a solvent, one or more co-solvents, an active agent, and optionally one or more of a buffer system, a tonicity adjusting agent, and a chelating agent as described herein. The method may include a sterilization step, such as a terminal sterilization step. Non-limiting examples of sterilization steps include autoclaving, sterile filtration, irradiation (e.g., using gamma and/or e-beam sterilization), and combinations thereof.

The present invention also provides for methods of treating or reducing the symptoms associated with a medical condition, the method including administering the composition of the present disclosure to a subject in need thereof. Examples of conditions to be treated include, but are not limited to, hypertension, hypertensive emergency, eclampsia, heart failure with reduced ejection fraction (HFrEF), and combinations thereof. Examples of methods of administration include subcutaneous, intracameral, intravenous, and intramuscular injection, infusion, intra-arterial administration, intracardiac injection, endotracheal administration, intraosseous administration, oral administration, topical administration, and as ophthalmic irrigation.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The following non-limiting examples illustrate particular embodiments of the compositions and processes as described herein. The examples are not meant to be comprehensive of the entire scope of the compositions and processes.

EXAMPLES

Example I: Storage Stability of 10 mg/mL Hydralazine Hydrochloride Compositions

First, four compositions of hydralazine hydrochloride were prepared by combining hydralazine hydrochloride with a solvent of water or water and propylene glycol as co-solvent, as shown in Table 2 below. In particular, Table 2 shows the concentration of propylene glycol in each composition in terms of % v/v and mg/mL.

TABLE 2

10 mg/mL Hydralazine Hydrochloride Compositions

| Com-position | propylene glycol % v/v | propylene glycol mg/mL | hydralazine hydrochloride (mg/mL) | Weight ratio of propylene glycol: hydralazine hydrochloride |
|---|---|---|---|---|
| 1 | 0 | 0 | 10 | — |
| 2 | 5 | 51.8 | 10 | 5.18:1 |
| 3 | 10 | 103.6 | 10 | 10.4:1 |
| 4 | 15 | 155.4 | 10 | 15.5:1 |

The four compositions were also compared with a commercially available composition, HydrALAZINE™ Hydrochloride Injection, USP provided by Akorn Operating Company LLC. HydrALAZINE™ Hydrochloride Injection, USP is available in a 1 mL vial for intravenous and intramuscular administration. HydrALAZINE™ Hydrochloride Injection, USP is a sterile, nonpyrogenic, colorless solution having 20 mg of hydralazine hydrochloride per vial.

To conduct the study, Compositions 1-4 and the commercially available composition (RLD) were first analyzed in order to determine an initial concentration of impurities. The compositions were analyzed using a gradient HPLC method with UV detection. A HPLC column with a C-18 polar stationary phase was used. The mobile phases were as shown in Table 3. Table 3 also shows the needle wash, seal wash, and diluent solutions used in the analysis.

TABLE 3

Solutions for Gradient HPLC Method

| Solution | Preparation |
|---|---|
| Mobile Phase A | Weigh and dissolve 0.34 g of potassium hydrogen phosphate in 1000 mL of Water. Adjust pH to 2.5 with dilute o-phosphoric acid. Mix well. |
| Mobile Phase B | 100% Methanol |
| Needle Wash | Prepare a 50:50 v/v Water/MeOH mixture and mix well. |
| Seal Wash | Prepare a 80:20 v/v Water/Methanol mixture and mix well. |
| Diluent | Adjust pH of water to 3.2 with dilute o-phosphoric acid. |

Table 4 shows the standards used in the analysis.

TABLE 4

Standards for Gradient HPLC Method

| Solution | Preparation |
|---|---|
| Stock Standard (SS) | Transfer 25 mg hydralazine hydrochloride into 50 mL volumetric flask. Add diluent and |

TABLE 4-continued

Standards for Gradient HPLC Method

| Solution | Preparation |
| --- | --- |
|  | sonicate to dissolve. Dilute to volume with additional diluent. |
| Working Standard (WS) | Dilute 5.0 mL Working Standard to 50.0 mL. Dilute to volume with diluent and mix well. |
| Stock Check Standard (SCS) | Repeat preparation for Stock Standard (SS) |
| Working Check Standard (WCS) | Repeat preparation for Working Standard (WS) |
| Bracketing Standard | Use the Working Standard solution. |

The chromatographic conditions used for the analysis are shown in Tables 5 and 6.

TABLE 5

Liquid Chromatography System and Chromatographic Conditions

| System | HPLC or equivalent |
| --- | --- |
| Column | Inertsil ODS-3V, 5 μm, 4.6 × 150 mm (UP): GL Sciences Cat. No 5020-01801 |
| Column Temperature | 30° C. ± 5° C. |
| Sample Temperature | 5° C. ± 5° C. |
| Injection Volume | 20 μl |
| Flow Rate | 1.0 mL/min |
| Detection | 230 nm |
| Mobile Phase A | pH 2.5 potassium phosphate monobasic |
| Mobile Phase B | Methanol |

| Gradient | Time (min) | % A | % B |
| --- | --- | --- | --- |
|  | 0.0 | 97 | 3 |
|  | 1.95 | 97 | 3 |
|  | 27 | 30 | 70 |
|  | 27.05 | 97 | 3 |
|  | 31 | 97 | 3 |

TABLE 6

Sample Sequence

| Number of Injections | Sample Name |
| --- | --- |
| 1 | Diluent |
| 1 | ID Solution |
| 6 | Working Standard (WS) |
| 1 | Check Standard (CS) |
| 1 | Blank |
| Up to 10 | Samples |
| 1 | Bracketing Standard (WS) |
| 1 | Diluent |

The system suitability requirements were as follows:
Blank chromatogram must show no peaks (≤0.5% of the main peak area) interfering with the peak of interest.
The USP Tailing Factor.
The RSD (%) based on 6 replicate injections of WS must be ≤5.0%.
The Check Standard Recovery for formaldehyde and acetaldehyde (Eq. 1) must be within the range 90-110%.

$$CS\ Recovery = \frac{R_{BS}}{R_{WS}} \times 100\%, \quad (1)$$

where $R_{BS}$ is the corresponding peak area from the Check Standard chromatogram and $R_{WS}$ is the average peak area based on the six replicate injections of the Working Standard.

The Bracketing Standard Recovery for formaldehyde and acetaldehyde (Eq. 2) must be within the range 90-110%.

$$CS\ Recovery = \frac{R_{BS}}{R_{WS}} \times 100\%, \quad (2)$$

where $R_{BS}$ is the corresponding peak area from the Bracketing Standard chromatogram and $R_{WS}$ is the average peak area based on the five replicate injections of the Working Standard.

Quantitation was accomplished by comparing corresponding peak areas from a Sample solution chromatogram to that of the external Reference Standard solution of known concentration. Table 7 shows the Relative Retention Time (RRT) for several unspecified related substances, also referred to as unknown impurities.

TABLE 7

Unknown Impurities in Hydralazine Hydrochloride Compositions

| Impurity | Approximate RRT |
| --- | --- |
| A | 0.349 |
| B | 1.183 |
| C | 1.310 |
| D | 2.195 |
| E | 2.242 |
| F | 2.325 |
| G | 2.369 |
| H | 2.477 |
| I | 3.548 |
| J | 3.678 |

Tables 8 and 9 show the initial impurity concentration expressed as % (w/w) of hydralazine hydrochloride observed in each composition.

TABLE 8

Initial Impurity Concentrations of Hydralazine Hydrochloride Compositions

| Composition | Phthalazone | 2-carboxybenzalehyde-2 | A | B | C |
| --- | --- | --- | --- | --- | --- |
| 1 | — | — | 0.0930 | — | — |
| 2 | — | — | 0.0953 | — | — |
| 3 | — | — | 0.0950 | — | — |
| 4 | — | — | 0.0905 | — | — |
| RLD | 0.0360 | 0.0046 | 0.0041 | 0.1473 | 0.0225 |

TABLE 9

Initial Impurity Concentrations of Hydralazine Hydrochloride Compositions

| Composition | E | F | G | H | I | J |
| --- | --- | --- | --- | --- | --- | --- |
| 1 | — | 0.0048 | — | — | 0.0208 | — |
| 2 | — | — | — | — | 0.0202 | — |

TABLE 9-continued

Initial Impurity Concentrations of Hydralazine Hydrochloride Compositions

| Composition | E | F | G | H | I | J |
|---|---|---|---|---|---|---|
| 3 | — | — | 0.0161 | — | 0.0380 | |
| 4 | — | — | 0.0259 | 0.0073 | 0.0418 | — |
| RLD | 0.0174 | — | 0.1083 | 0.0108 | 0.0044 | 0.4832 |

The compositions were then stored for two months at a temperature of 60° C. During the two-month period, the compositions were tested at the start of storage (i.e., initial) and at day one, day three, week one, week two, and week three to determine pH, concentration of hydralazine hydrochloride (as a percentage of the label claim), the total specified impurities, and the total unspecified impurities. The results of this study are shown in Tables 10-13 below.

TABLE 10 pH of Hydralazine Hydrochloride Compositions
pH

| Composition | 1 | 2 | 3 | 4 | RLD |
|---|---|---|---|---|---|
| Initial | 4.09 | 4.09 | 4.07 | 4.06 | — |
| Day 1 | 4.27 | 4.20 | 4.20 | 4.15 | — |
| Day 3 | 4.74 | 4.59 | 4.54 | 4.61 | 3.71 |
| Week 1 | 4.19 | 4.14 | 4.12 | 4.01 | — |
| Week 2 | 4.01 | 3.97 | 3.86 | 3.67 | 3.53 |
| Week 4 | 3.81 | 3.76 | 3.52 | 3.24 | 3.34 |

TABLE 11

Hydralazine Hydrochloride Concentration in Compositions
Hydralazine Hydrochloride
% Label Claim

| Composition | 1 | 2 | 3 | 4 | RLD |
|---|---|---|---|---|---|
| Initial | 98.56 | 100.05 | 100.28 | 101.22 | 101.04 |
| Day 1 | 100.29 | 100.99 | 100.88 | 101.28 | 101.61 |
| Day 3 | 100.51 | 100.09 | 99.75 | 100.98 | 102.63 |
| Week 2 | 98.02 | 99.25 | 99.20 | 99.10 | 99.19 |
| Week 4 | 96.33 | 96.57 | 96.12 | 96.93 | 95.36 |
| 2 Months | | 92.95 | 75.1262 | 67.0217 | 94.0661 |

TABLE 12

Specified Impurities in Hydralazine Hydrochloride Compositions
Hydralazine Hydrochloride Impurities—Total Specified
% (w/w) of Hydralazine Hydrochloride

| Composition | 1 | 2 | 3 | 4 | RLD |
|---|---|---|---|---|---|
| Initial | 0.02 | 0.00 | 0.00 | 0.00 | 0.04 |
| Day 1 | 0.27 | 0.27 | 0.26 | 0.26 | 0.40 |
| Day 3 | 0.13 | 0.12 | 0.13 | 0.11 | 0.14 |
| Week 2 | 0.51 | 0.48 | 0.48 | 0.55 | 0.41 |
| 1 Month | 1.06 | 0.91 | 0.97 | 0.99 | 0.72 |
| 2 Months | — | 7.5494 | 37.4539 | 57.0113 | 4.8599 |

TABLE 13

Unspecified Impurities in Hydralazine Hydrochloride Compositions
Hydralazine Hydrochloride Impurities Total Unspecified
% (w/w) of Hydralazine Hydrochloride

| Composition | 1 | 2 | 3 | 4 | RLD |
|---|---|---|---|---|---|
| Initial | 0.12 | 0.12 | 0.15 | 0.17 | 0.80 |
| Day 1 | 0.12 | 0.17 | 0.21 | 0.27 | 0.92 |
| Day 3 | 0.13 | 0.23 | 0.36 | 0.44 | 0.98 |
| Week 2 | 0.34 | 0.46 | 0.67 | 0.99 | 0.75 |
| 1 Month | 1.30 | 1.42 | 1.97 | 3.07 | 3.37 |
| 2 Months | — | 2.5749 | 8.2663 | 10.6096 | 3.5074 |

Figure 1:
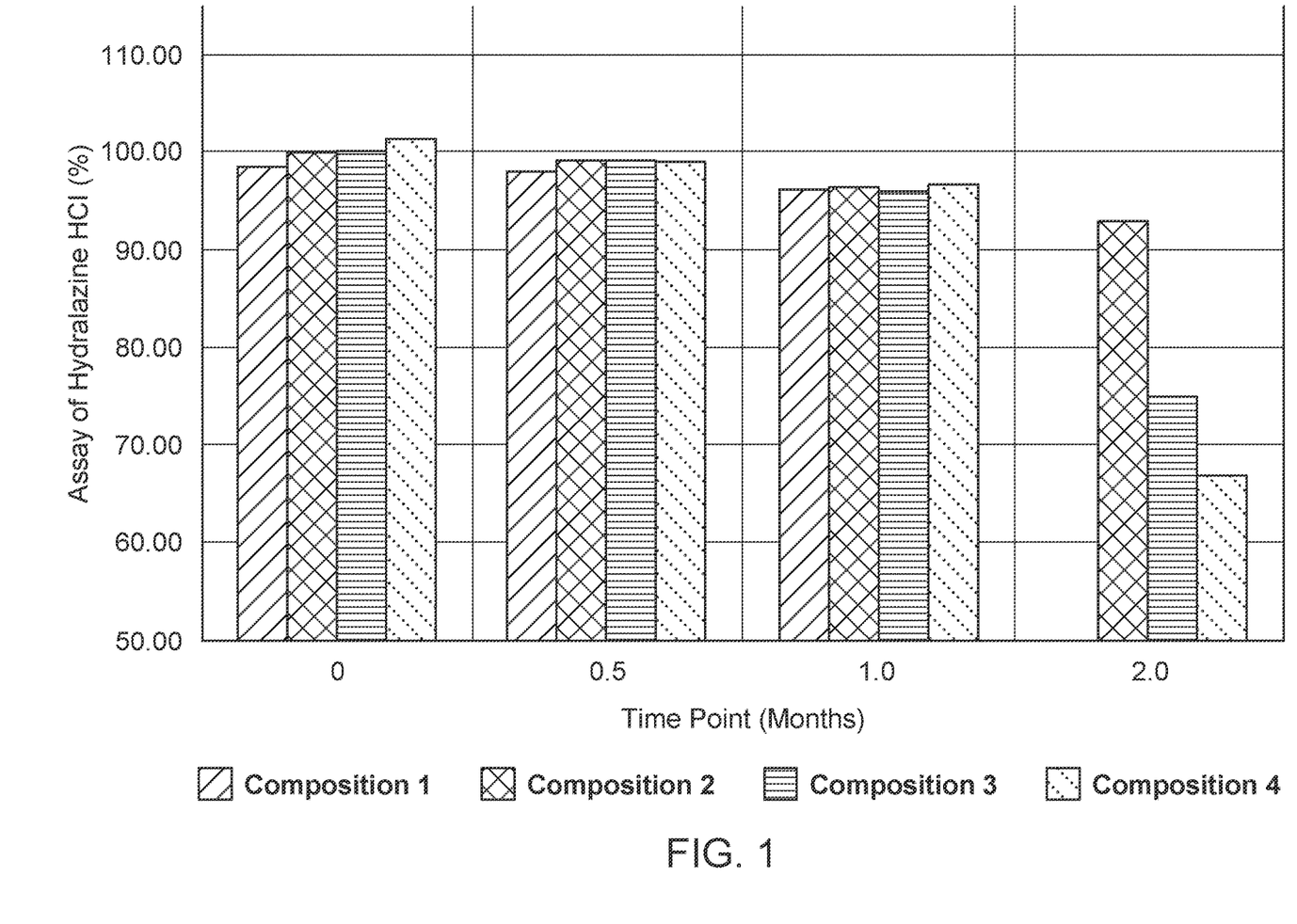
FIG. 1 shows the data from Table 4 (i.e., the concentration of hydralazine hydrochloride as a percentage of the label claim) in graphical form.

FIG. 1 shows the data from Table 11 (i.e., the concentration of hydralazine hydrochloride as a percentage of the label claim) in graphical form. As shown in FIG. 1, at a co-solvent to hydralazine weight ratio of about 5:1, composition 2 showed unexpectedly good stability when compared with the compositions having a higher ratio, which exhibited a precipitous decline in stability at 2 months.

Example II: Storage Stability of 20 mg/mL Hydralazine Hydrochloride Compositions First, four compositions of hydralazine hydrochloride were prepared by combining hydralazine hydrochloride with a solvent of water or water and propylene glycol as co-solvent, as shown in Table 14 below.

TABLE 14

20 mg/mL Hydralazine Hydrochloride Compositions

| Composition | propylene glycol % v/v | propylene glycol mg/mL | hydralazine hydrochloride (mg/mL) | Weight ration of propylene glycol: hydralazine hydrochloride |
|---|---|---|---|---|
| 5 | 0 | 0 | 20 | — |
| 6 | 5 | 51.8 | 20 | 2.59:1 |
| 7 | 10 | 103.6 | 20 | 5.18:1 |
| 8 | 15 | 155.4 | 20 | 7.77:1 |

The four compositions were also compared with HydrA-LAZINE™ Hydrochloride Injection, USP, as described in Example I.

Compositions 5-8 and the commercially available composition (RLD) were then analyzed as described in Example I. Tables 15 and 16 shows the initial impurity concentration for each of the solutions, expressed as % (w/w) of hydralazine hydrochloride.

TABLE 15

Initial Impurity Concentrations of Hydralazine Hydrochloride Compositions

| Composition | Phthalazone | 2-carboxybenzalehyde-2 | A | B | C |
|---|---|---|---|---|---|
| 5 | — | — | 0.0969 | — | — |
| 6 | — | — | 0.0921 | — | — |
| 7 | — | — | 0.0934 | — | — |
| 8 | — | — | 0.0962 | — | — |
| RLD | 0.0360 | 0.0046 | 0.0041 | 0.1473 | 0.0225 |

TABLE 16

Initial Impurity Concentrations of Hydralazine Hydrochloride Compositions

| Composition | E | F | G | H | I | J |
|---|---|---|---|---|---|---|
| 5 | — | — | — | — | 0.0163 | — |
| 6 | — | 0.0050 | — | — | 0.0299 | — |
| 7 | — | — | — | — | 0.0345 | — |
| 8 | — | — | — | — | 0.0407 | — |
| RLD | 0.0174 | — | 0.1083 | 0.0108 | 0.0044 | 0.4832 |

The compositions were then stored for two months at a temperature of 60° C. During the two-month period, the compositions were analyzed initially and at day one, day three, week one, week two, and week three to determine pH, concentration of hydralazine hydrochloride (as a percentage of the label claim), the total specified impurities, and the total unspecified impurities. The results of this study are shown in Tables 17-20 below.

TABLE 17 pH of Hydralazine Hydrochloride Compositions
pH

| Composition | 5 | 6 | 7 | 8 | RLD |
|---|---|---|---|---|---|
| Initial | 4.02 | 4.03 | 4.00 | 3.98 | — |
| Day 1 | 4.12 | 4.07 | 4.07 | 4.04 | — |
| Day 3 | 4.35 | 4.33 | 4.32 | 4.32 | 3.71 |
| Week 1 | 4.06 | 3.99 | 3.98 | 3.91 | — |
| Week 2 | 3.97 | 3.77 | 3.84 | 3.62 | 3.53 |
| Week 4 | 3.74 | 3.48 | 3.51 | 3.25 | 3.34 |

TABLE 18

Hydralazine Hydrochloride Concentration in Compositions
Hydralazine Hydrochloride
% Label Claim

| Composition | 5 | 6 | 7 | 8 | RLD |
|---|---|---|---|---|---|
| Initial | 100.07 | 100.70 | 101.10 | 100.38 | 101.04 |
| Day 1 | 101.11 | 101.22 | 102.06 | 101.88 | 101.61 |
| Day 3 | 101.06 | 101.14 | 102.11 | 100.74 | 102.63 |
| Week 2 | 98.05 | 97.53 | 99.22 | 99.13 | 99.19 |
| Week 4 | 95.85 | 96.71 | 96.42 | 97.73 | 95.36 |
| 2 Months | | 91.34 | 92.5387 | 90.8143 | 94.0661 |

TABLE 19

Specified Impurities in Hydralazine Hydrochloride Compositions
Hydralazine Hydrochloride Impurities—Total Specified

| Composition | 5 | 6 | 7 | 8 | RLD |
|---|---|---|---|---|---|
| Initial | 0.00 | 0.00 | 0.00 | 0.00 | 0.04 |
| Day 1 | 0.23 | 0.22 | 0.22 | 0.21 | 0.40 |
| Day 3 | 0.11 | 0.10 | 0.11 | 0.11 | 0.14 |
| Week 2 | 0.39 | 0.40 | 0.39 | 0.46 | 0.41 |
| 1 Month | 0.76 | 0.79 | 0.74 | 0.85 | 0.72 |
| 2 Months | | 7.7457 | 7.1564 | 12.0854 | 4.8599 |

TABLE 20

Unspecified Impurities in Hydralazine Hydrochloride Compositions
Hydralazine Hydrochloride Impurities Total Unspecified

| Composition | 5 | 6 | 7 | 8 | RLD |
|---|---|---|---|---|---|
| Initial | 0.11 | 0.13 | 0.13 | 0.14 | 0.80 |
| Day 1 | 0.12 | 0.15 | 0.17 | 0.21 | 0.92 |
| Day 3 | 0.11 | 0.22 | 0.27 | 0.29 | 0.98 |
| Week 2 | 0.32 | 0.51 | 0.50 | 0.64 | 0.75 |
| 1 Month | 1.41 | 1.80 | 1.63 | 2.01 | 3.37 |
| 2 Months | — | 3.6253 | 2.5906 | 3.0512 | 3.5074 |

Figure 2:
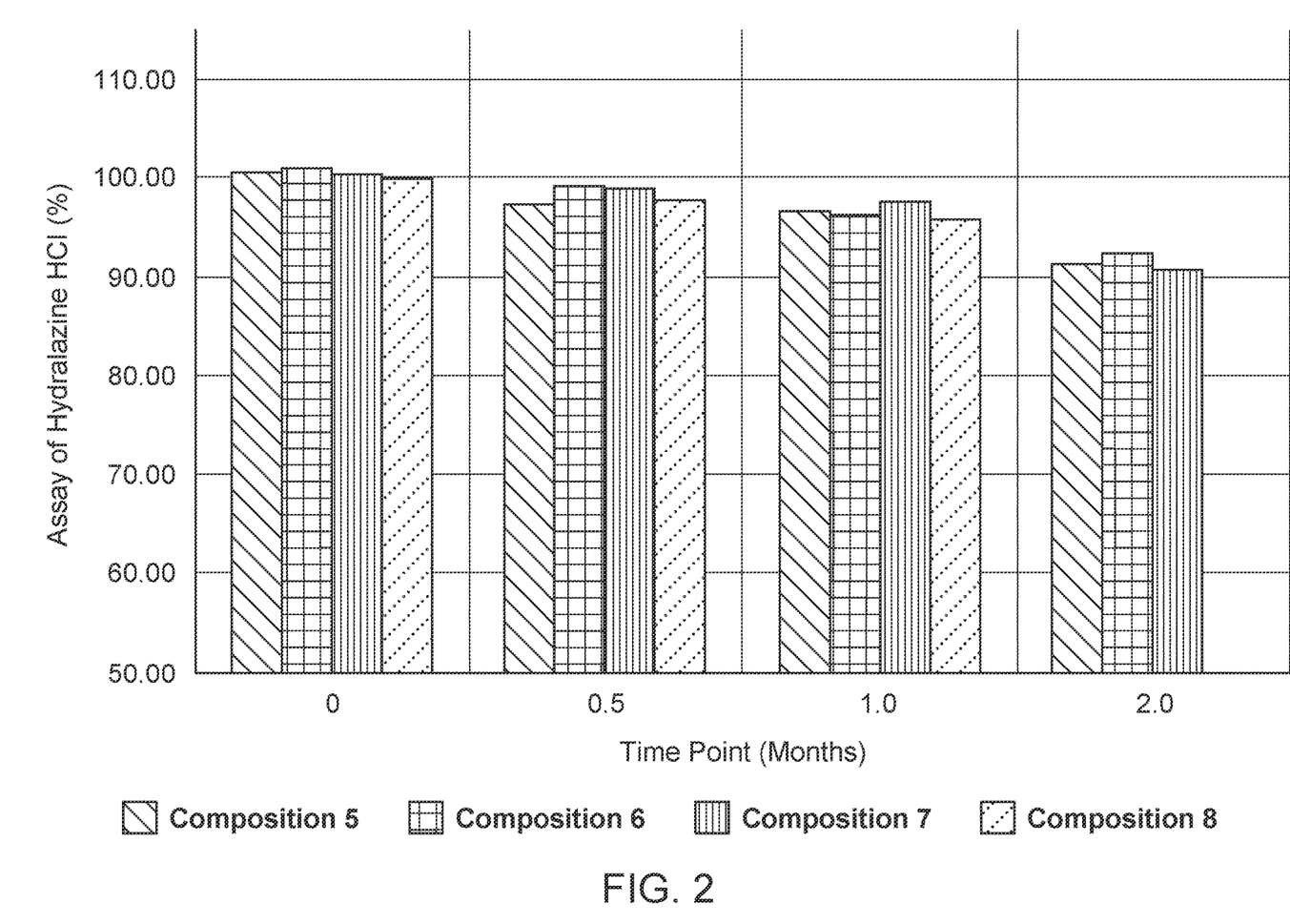
FIG. 2 shows the data from Table 9 (i.e., the concentration of hydralazine hydrochloride as a percentage of the label claim) in graphical form.

FIG. 2 shows the data from Table 18 (i.e., the concentration of hydralazine hydrochloride as a percentage of the label claim) in graphical form. As shown in FIG. 2, the stability was substantially the same for all compositions.

Based on the results shown in FIGS. 1 and 2, it was determined that a formulation having a relatively low concentration of hydralazine hydrochloride (e.g., a concentration suitable for a ready-to-use composition) at a certain co-solvent to hydralazine weight ratio surprisingly exhibited a stability comparable to more concentrated formulations.

Example III: 10 mg/mL Hydralazine Hydrochloride Compositions

The compositions of hydralazine hydrochloride shown in Table 21 are further preferred embodiments. The compositions in Table 21 include hydralazine hydrochloride in a solvent of water and a co-solvent.

TABLE 21

10 mg/mL Hydralazine Hydrochloride Compositions

| Composition | Co-solvent | Co-solvent concentration (mg/mL) | hydralazine hydrochloride (mg/mL) |
|---|---|---|---|
| 9 | Polyethylene glycol | 50 | 10 |
| 10 | Ethylene glycol | 50 | 10 |
| 11 | Isopropanol | 50 | 10 |
| 12 | Ethanol | 50 | 10 |
| 13 | Vegetable oil | 50 | 10 |

What is claimed is:

1. A sterile, ready-to-use pharmaceutical composition comprising:
   hydralazine and/or a salt thereof at a concentration of about 10 mg/mL, and
   a solvent comprising a co-solvent, wherein the solvent comprises water and the co-solvent comprises propylene glycol,
   wherein the co-solvent and the hydralazine and/or salt thereof are provided at a weight ratio of no more than about 7.5:1, and wherein the hydralazine and/or salt thereof has a change in concentration of no more than about 10% after 2 months of storage at 60° C.

2. The composition of claim 1, wherein the weight ratio is no more than about 6:1.

3. The composition of claim 1, wherein the co-solvent is provided at a concentration of about 5% v/v.

4. The composition of claim 1, further comprising a buffer.

5. The composition of claim 4, wherein the buffer comprises a citrate buffer, a tartrate buffer, and/or an acetate buffer.

6. The composition of claim 1, further comprising a chelating agent.

7. The composition of claim 6, wherein the chelating agent is selected from the group consisting of ethylenediaminetetraacetic acid, ethylene glycol-bis(β-aminoethyl ether)-N,N,N',N'-tetraacetic acid, and penta(carboxymethyl) diethylenetriamine.

8. The composition of claim 1, further comprising a tonicity agent.

9. The composition of claim 8, wherein the tonicity agent comprises a pharmaceutically acceptable salt.

10. The composition of claim 1, wherein the composition is provided in a bag.

11. The composition of claim 1, wherein the composition is provided in a bottle.

12. The composition of claim 1, wherein the hydralazine and/or salt thereof has a change in concentration of no more than about 8% after 2 months of storage at 60° C.

13. A pre-filled syringe comprising a sterile, ready-to-use pharmaceutical composition, the composition comprising:
   hydralazine and/or a salt thereof at a concentration of about 10 mg/mL, and
   a solvent comprising a co-solvent, wherein the solvent comprises water and the co-solvent comprises propylene glycol,
   wherein the co-solvent and the hydralazine and/or salt thereof are provided at a weight ratio of no more than about 7.5:1, and wherein the hydralazine and/or salt thereof has a change in concentration of no more than about 10% after 2 months of storage at 60° C.

14. The pre-filled syringe of claim 13, wherein the pre-filled syringe comprises between about 1 mL and 5 mL of the composition.

15. The pre-filled syringe of claim 13, wherein the weight ratio is no more than about 6:1.

16. The pre-filled syringe of claim 13, wherein the co-solvent is provided at a concentration of about 5% v/v.

17. A method of treating hypertension comprising administering to a subject in need thereof a sterile, ready-to-use pharmaceutical composition, the composition comprising:
   hydralazine and/or a salt thereof at a concentration of about 10 mg/mL, and
   a solvent comprising a co-solvent, wherein the solvent comprises water and the co-solvent comprises propylene glycol,
   wherein the co-solvent and the hydralazine and/or salt thereof are provided at a weight ratio of no more than about 7.5:1, and wherein the hydralazine and/or salt thereof has a change in concentration of no more than about 10% after 2 months of storage at 60° C.

18. The method of claim 17, wherein the administering is performed by direct injection from a pre-filled syringe.

* * * * *